US009101795B2

(12) United States Patent
Anderson

(10) Patent No.: US 9,101,795 B2
(45) Date of Patent: Aug. 11, 2015

(54) BRAIDED GOGGLE STRAP

(75) Inventor: Lynne Anderson, Greenwich, CT (US)

(73) Assignee: SMACK SWIM, LLC, Old Greenwich, CT (US)

( * ) Notice: Subject to any disclaimer, the term of this patent is extended or adjusted under 35 U.S.C. 154(b) by 68 days.

(21) Appl. No.: 13/507,157

(22) Filed: Jun. 8, 2012

(65) Prior Publication Data

US 2012/0311773 A1    Dec. 13, 2012

Related U.S. Application Data

(60) Provisional application No. 61/495,510, filed on Jun. 10, 2011.

(51) Int. Cl.
*A61F 9/02* (2006.01)
*A63B 33/00* (2006.01)

(52) U.S. Cl.
CPC ............ *A63B 33/002* (2013.01); *A63B 2209/02* (2013.01); *Y10T 24/13* (2015.01); *Y10T 24/1371* (2015.01); *Y10T 24/1397* (2015.01); *Y10T 24/1648* (2015.01)

(58) Field of Classification Search
CPC .......... G02C 3/003; G02C 11/02; G02C 5/00; G02C 3/006; A63B 33/002; A63B 2209/02; A63B 2033/004; A63B 2033/006; A63B 2033/008; A63B 33/00
USPC ......... 24/3.1, 3.13, 3.4, 34, 3.3, 712.1, 712.2; 351/156, 157; 2/410, 417–424, 425, 2/452
See application file for complete search history.

(56) References Cited

U.S. PATENT DOCUMENTS

| 1,948,844 | A | * | 2/1934 | Dawes .......................... 24/715.3 |
| 2,660,092 | A | | 11/1953 | Bloom |
| 3,059,518 | A | * | 10/1962 | Nelson ................................ 87/2 |
| 3,397,026 | A | | 8/1968 | Spina |
| 4,133,604 | A | * | 1/1979 | Fuller ............... 351/123 |
| 4,657,364 | A | * | 4/1987 | Murrell ......................... 351/156 |
| 4,692,002 | A | * | 9/1987 | Meistrell ....................... 351/156 |
| 4,783,164 | A | | 11/1988 | Heiberger |
| 4,881,803 | A | * | 11/1989 | Giles et al. ..................... 351/156 |
| 4,922,581 | A | * | 5/1990 | Wilson ................................ 24/36 |
| 4,953,967 | A | | 9/1990 | Somerville |
| 4,967,454 | A | * | 11/1990 | Elieff ........................... 24/712.1 |
| 5,015,085 | A | * | 5/1991 | May ................................ 351/43 |
| 5,313,671 | A | | 5/1994 | Flory |
| 5,390,373 | A | | 2/1995 | Flory |
| 5,541,676 | A | | 7/1996 | Pallat |
| 5,593,024 | A | * | 1/1997 | Seiler ................................ 206/5 |

(Continued)

*Primary Examiner* — Robert J Sandy
*Assistant Examiner* — Louis Mercado
(74) *Attorney, Agent, or Firm* — Vaughn Marquis, Esq.

(57) ABSTRACT

A braided goggle strap for use with a pair of swimming goggles includes a plurality of bands that are braided together to form a flat, braided goggle strap. Each of the plurality of bands includes an elastic material this is protected by a resilient fabric material to provide superior mechanical properties that results in even stress distribution and minimal sinusoidal stress when worn by a user. The composite reinforcement of the braided goggle strap also provides added comfort. The braided goggle strap includes a spring-biased fastener for adjustably attaching the braided strap onto a user's head, includes eye loops to more easily thread the braided goggle strap through apertures provided on a pair of swimming goggles, and comes in a variety of different colors.

19 Claims, 4 Drawing Sheets

(56) References Cited

U.S. PATENT DOCUMENTS

| | | | |
|---|---|---|---|
| 5,655,263 A * | 8/1997 | Stoller | 24/3.3 |
| 5,664,291 A * | 9/1997 | Stoller | 24/3.3 |
| 5,857,221 A | 1/1999 | Geneve et al. | |
| 5,926,855 A | 7/1999 | Brodbeck | |
| 6,092,897 A | 7/2000 | Smerdon, Jr. | |
| 6,941,619 B2 * | 9/2005 | Mackay et al. | 24/3.3 |
| 2006/0272636 A1 | 12/2006 | Orem et al. | |
| 2013/0162941 A1 * | 6/2013 | Johnson et al. | 351/157 |

* cited by examiner

BRAIDED GOGGLE STRAP

CROSS-REFERENCE TO RELATED APPLICATION

This application claims priority to U.S. Provisional Patent Application Ser. No. 61/495,510 filed Jun. 10, 2011, the subject matter of the provisional patent application is incorporated herein in the entirety.

FIELD OF THE INVENTION

The present invention relates to accessories for use with goggles. More particularly, the present disclosure relates to a braided goggle strap including a plurality of bands braided together to form a resilient, braided goggle strap including eye loops disposed at opposite ends of the braided goggle strap for attaching the strap to a pair of swimming goggles. The braided goggle strap also includes a spring-biased fastener for adjustably attaching the strap comfortably onto a user's head, and comes in a variety of different colors to help locate and identify swimming goggles via, the strap.

BACKGROUND OF THE INVENTION

There are a variety of goggles available on the market today that are designed to help protect the eyes of a user when engaging in certain physical activities. For example, many individuals routinely wear goggles when skiing, riding motorcycle, and when participating in certain sports. Employees working in hazardous areas also wear goggles to help protect their eyes from injury, dust and debris, and from exposure to chemicals or the like. Such goggles typically include a frame designed to overlay both eyes of an individual, a single plastic shield attached to the frame, and an adjustable strap affixed to opposite ends of the frame for securing the protective goggles onto the head of a user.

Other types of goggles include swimming goggles that are generally worn by professional and amateur swimmers alike. Swimming goggles are often worn by swimmers to protect the eyes when swimming in pools, lakes, ponds or rivers, and to allow a swimmer to open his or her eyes when navigating under water. Swimming goggles protect the individual's eyes from dirt, and other natural debris found in natural water ways, and from chlorine and other harsh chemicals typically used in public and private pools. Generally, swimming goggles include a pair of eye cups, a rubber strap attached to opposite ends of the eye cups, and a buckle for adjusting the length of the rubber strap to accommodate a number of individuals having different head sizes. The eye cups are dimensionally sized to cover both eyes of a swimmer and are either molded as one unit, or separately constructed and attached together via, a nose bridge. A foam pad is often disposed along the peripheral edge of each eye cup to provide comfort around the area of the eyes. Conventional swimming goggles typically come in a variety of different colors, shapes and designs and often include transparent or tinted eye cups.

The rubber or elastic strap used on conventional swimming goggles provides various drawbacks. Most rubber straps used with swimming goggles include a flat band that is constructed from a thin rubber material. The rubber strap is designed to compress tightly against a swimmer's hair and outer surface area of the head making it difficult for a swimmer to position the strap onto the head, or providing discomfort to a wearer during extended use. The flat rubber band often twists forcing the swimmer to repeatedly make adjustments to orient the band in a flat, comfortable position. A user often attempts to untwist the elastic strap when the swimming goggle is already positioned onto the user's head. In doing so, the wearer typically pinches the band and pulls the elastic band away from the head in an effort to straighten the elastic band to provide a more comfortable fit. As a result of the rubber strap sticking to the user's hair, the individual ends up pulling his or her hair causing pain and discomfort.

Another drawback of conventional goggle straps is that most goggle straps include a slider or buckle that are used to make necessary adjustments to the length of the strap. To achieve a desired fit and to prevent the swimming goggles from falling off, the user must slide the strap through designated slots provided in the slider or buckle to tighten the strap. In many cases, a wearer must repeatedly remove the pair of swimming goggles from his or her head to make adjustments. Most traditional swimming goggles that include adjustable rubber straps having sliders or buckles that prevent a wearer from easily and quickly adjusting the length of the rubber strap while wearing the swimming goggles. The traditional design of sliders and buckles also frustrates the ability for parents to quickly make adjustments to the rubber strap while the swimming goggles are fitted on a child's head. The child often becomes impatient or experiences discomfort as the parent repeatedly removes the swimming goggles to make adjustments. Further, the thin rubber material used in constructing the rubber strap becomes frail over time as a result of wear and tear and prolonged exposure to chemicals and sunlight. The properties of the rubber strap break down over time and the strap eventually breaks during use.

Another disadvantage provided by conventional swimming goggle straps is that most straps are similar in appearance. Typical swimming goggle straps often comprise a light or dark shade of grey or black. Should the swimming goggles fall off during use and become lost, it would be difficult for a person to identify the goggles when found. Also, swimming goggles having differently sized goggle straps may also be hard to distinguish from one another. Individuals having different head sizes may wish to quickly differentiate between swimming goggles having differently sized goggle straps. Distinguishable features may be beneficial where a group of swimmers are concentrated in one local.

In an effort to address some of the disadvantages of the prior art, some swimming goggle straps have implemented the use of a shock cord or a tubular bungee cord. Generally, the tubular bungee cord includes a single rubber cord or a plurality of individual rubber cords or strands assembled together to provide a round elastic core. The core can be covered with a stretchable fabric or mesh material to help protect the tubular elastic core. The tubular bungee cord is adapted for used with a pair of swimming goggles and often includes a cord lock for adjusting the length of the tubular bungee cord.

The conventional bungee cord design also includes certain drawbacks. The tubular dimension of the bungee cord often results in the bungee cord rolling along the user's head. As the tubular bungee cord rolls along the outer surface of a wearer's head, the cord becomes misaligned and pulls on one or both sides of the swimming goggles. The wearer must correct the rolling effect by repeatedly situating the tubular bungee cord in place around the head. In an effort to prevent rolling, the user tightens the cord around the head causing not only more stress and strain on the bungee cord itself, but greater discomfort to the wearer as the cord constricts tightly around the user's head and pulls even further on the swimming goggles. Thus, the tubular bungee cord results in a goggle strap that provides an uneven stress distribution, an increased sinusoidal stress or strain, poor sheer resistance, and limited strength in the primary loading direction thereby providing uneven distribution and discomfort to a user.

What is desired is a braided goggle strap for use with swimming goggles that is quickly and easily adjustable when worn on a user, inexpensive, and comfortable to wear. What is further desired is a braided goggle strap that includes superior mechanical properties, includes even stress distribution and minimal sinusoidal stress to provide comfort when worn on a user's head, and includes distinguishable features to help differentiate one swimming goggle strap from another.

SUMMARY OF THE INVENTION

A first aspect of the present invention provides a braided goggle strap comprising: a plurality of bands braided together to form a braided elongated body having a first end and a second end opposite the first end, where each of the plurality of bands include a resilient material enclosed in a resilient fabric material; a first band extension being a portion of one of the plurality of bands and extending a length from the first end; a second band extension being a portion of another one of the plurality of bands and extending a length from the second end, where the first band extension is folded over and attached to the first end forming a first eye loop, and the second band extension is folded over and attached to the second end forming a second eye loop, where each of the eye loops and each of the plurality of bands have a width dimensioned to fit within a pair of apertures provided on a pair of goggles, and a bias fastener operated to releasably grip onto the plurality of bands for securely attaching the braided goggle strap onto a user's head.

Preferably, plurality of bands include a first band, a second band, and a third band where each band comprises a flat geometric shape, though other geometric shapes are possible. The resilient material includes any one of natural rubber, synthetic rubber, latex, nylon, stretch fabric (elastomerics), blended rubber with polyester, blended rubber with cotton, blended rubber with nylon or any combination thereof. The resilient fabric covering includes any one of woven or non-woven material, cotton, polyester, nylon, poly-vinyl chloride (PVC), rayon, microfiber, acrylic, acetate, wool, leather, vinyl, or any other suitable fabric that is able to withstand wear and tear and repeated stretching over time.

Advantageously, the bias fastener includes an outer body having an opening and an outer body aperture, an inner body dimensioned to slideably fit within the opening of the outer body and including an inner body aperture, and a bias member disposed within the opening and between the outer body and the inner body, where the bias member operatively separates the outer body from the inner body to misalign the body apertures to securely grip the plurality of bands when the plurality of bands are inserted through the body apertures, and where the bias fastener is operated to align the body apertures to release the grip on the plurality of bands allowing the plurality of bands to slide freely through the body apertures.

In one aspect, each of the band extensions optionally includes a rigid member that is attached to, or enclosed within each of the band extensions. The resilient fabric covering includes the same color or a variety of different colors to form a braided goggle strap including a plurality of bands with resilient fabric covering having different colors.

Another aspect of the present invention provides, a braided swimming goggle strap for use with swimming goggles, said braided swimming goggle strap comprising: a plurality of strands of material interlaced together to form a braided goggle strap having two opposite ends, where each of the plurality of strands of material include a resilient material; a first guide formed from a portion of one of the plurality of strands of material and extending outwards a length from one of the two opposite ends; a second guide formed from a portion of another one of the plurality of strands of material and extending outwards a length from another of the two opposite ends, where the plurality of strands of material are combined to thread through a pair of apertures provided on a pair of swimming goggles to form a first attachment strap and a second attachment strap, and a fastener operated to releasably grip onto the braided swimming goggle strap for securely attaching the braided swimming goggle strap onto a user's head.

Preferably, each of the plurality of strands of material further includes a resilient fabric material, where the resilient fabric material is attached to, or completely encases each of the plurality of strands of material. In one alternative embodiment, each guide includes a rigid member.

Yet another aspect of the present invention provides, a pair of goggles comprising; at least one eye shield adapted to cover an individual's eyes, and including apertures provided at opposite edges of the at least one eye shield; a plurality of bands braided together to form a braided goggle strap having a first end and a second end opposite the first end, where each of the plurality of bands include a stretchable material and a resilient fabric covering; a first band extension being a portion of one of the plurality of bands and extending a length from the first end; a second band extension being a portion of another one of the plurality of bands and extending a length from the second end, where the first band extension is folded over and attached to the first end forming a first eye loop, and the second band extension is folded over and attached to the second end forming a second eye loop, and a fastener operated to releasably grip the braided goggle strap for securely attaching the pair of goggles onto a user's head.

Preferably, the at least one eye shield includes a first eye shield joined to a second eye shield via, a nose bridge, and the apertures include a first aperture provided at an outer edge of the first eye shield and a second aperture provided at an outer edge of the second eye shield. The braided goggle strap is threaded through the apertures to form a first attachment strap and a second attachment strap for attaching the goggles onto a user's head.

These and other advantages of the invention will be further understood and appreciated by those skilled in the art by reference to the following written specifications, claims, and appended drawings.

BRIEF DESCRIPTION OF THE DRAWINGS

The invention will now be described, by way of example, with reference to the accompanying drawings, in which.

DETAILED DESCRIPTION OF THE INVENTION

One or more embodiments of the present invention are disclosed herein. The embodiments are merely exemplary of the invention that may be embodied in various and alternative forms. It is noted that the various views, features, elements, and dimensions of the disclosed exemplary embodiments are not necessarily to scale, and may be enlarged, exaggerated, minimized, or sectionalized for clarity. Thus, specific structural and functional details, dimensions, shapes, or configurations disclosed herein are not limiting but serve as a basis for teaching a person of ordinary skill in the art the described and claimed features of the one or more embodiments of the present invention.

Figure 1:
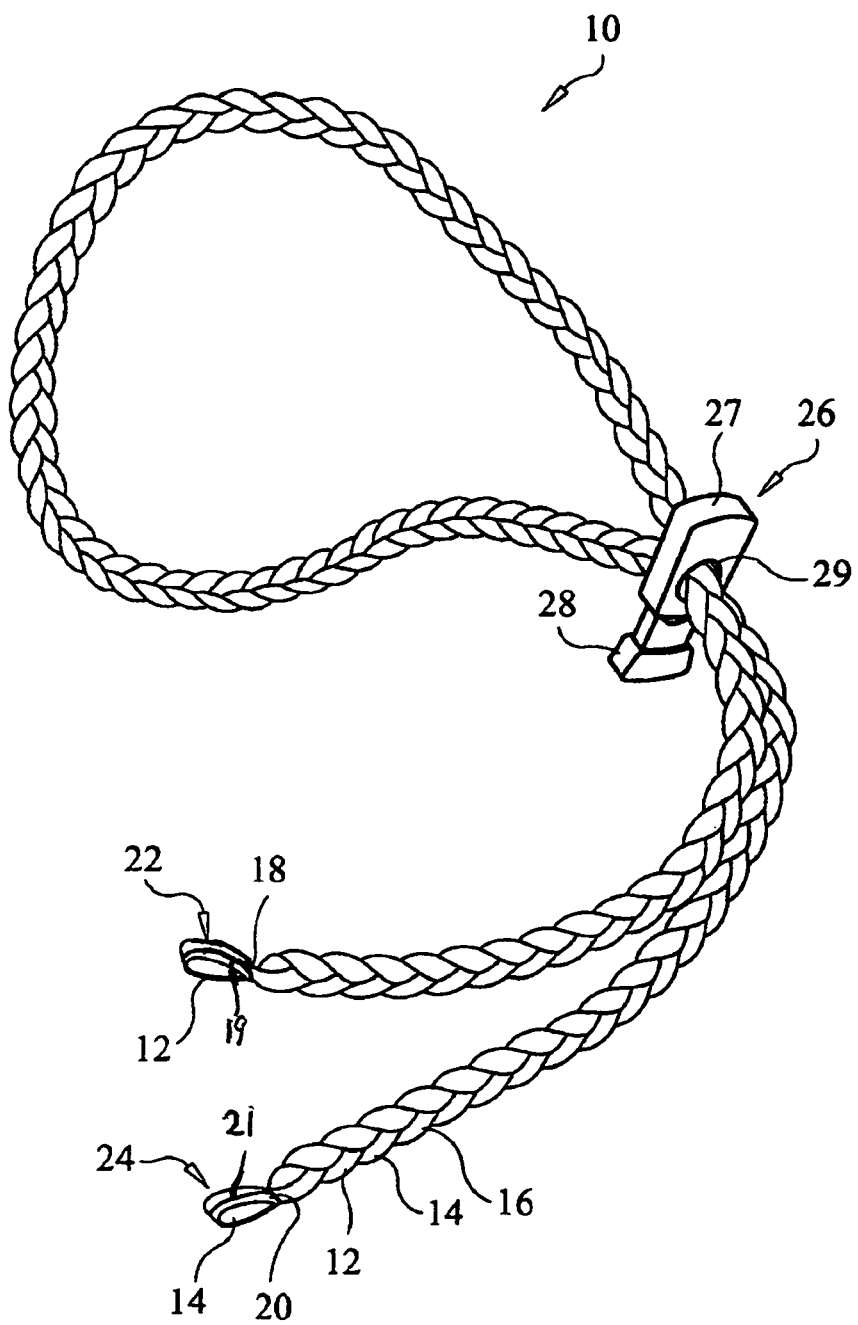
FIG. 1 is a perspective view of a braided goggle strap, in accordance with the present invention.

Referring now to the drawings wherein like elements are represented by like numerals throughout, there is shown in FIG. 1 a perspective view of a braided goggle strap 10 in accordance with the embodiment of the present invention. The braided goggle strap 10 of the present invention is shown for use with a pair of swimming goggles 30 for illustrative purposes only. It will be understood that the braided goggle strap 10 may be adapted for use with a variety of different goggles, including but not limited, to goggles used for working, gardening, enjoying hobbies like wood carving, participating in sports such as skiing, fishing, or the like, and riding or operating motor operated vehicles such as motorcycles, ATVs or snowmobiles.

In one embodiment of the present invention, the braided goggle strap 10 includes a plurality of bands 12, 14, 16 braided together to form a resilient or stretchable, flat, braided goggle strap 10 having a first end 18 and a second end 20, opposite the first end 18. In one exemplary embodiment, the plurality of bands comprises a first band 12, a second band 14 and a third band 16, each band having a preselected length. In a preferred embodiment, each band 12, 14, 16 comprises a flat geometric shape, though other geometric shapes may be used. The word "band" as used herein is not deemed to be limiting on the present invention and is used merely to represent a length of material. Although the exemplary embodiment shows the use of three bands 12, 14, 16, it will be noted that the braided goggle strap 10 may include an N number of bands that are braided together to form a strong, braided goggle strap 10. Each band 12, 14, 16 may include a single material or a plurality of different materials that are integrally formed, glued, molded, woven, knitted or braided together to form a single band 12, 14, 16. Also, each band 12, 14, 16 may include a single ply or multi-ply layer of the same or different materials. For example, each of the plurality of bands 12, 14, 16 may include a first rubber layer and a second rubber layer, or a polyester layer adhered to a rubber layer, or a rubber layer sandwiched between a top polyester layer and a bottom polyester layer. Preferably, bands 12, 14, 16 comprise a resilient or stretchable material that includes, but is not limited to, natural rubber, synthetic rubber, latex, nylon, stretch fabric (elastomerics), blended rubber with polyester, blended rubber with cotton, blended rubber with nylon, any combination thereof, or any other suitable materials that may be formed into an elongated body that can repeatedly stretch and return to a non-stretched state.

Figure 1A:
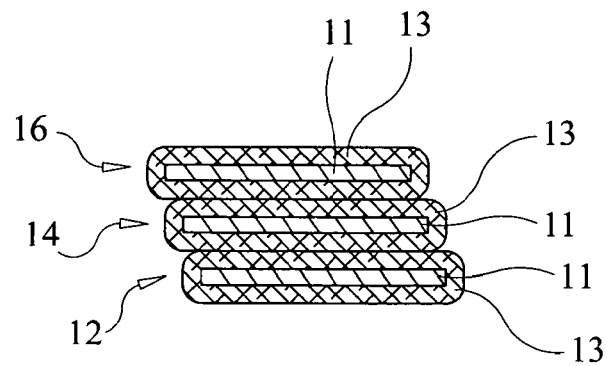
FIG. 1A is a cross-sectional view of the braided goggle strap of FIG. 1, showing a plurality of bands where each band includes an elastic material covered or enclosed with a resilient fabric material, in accordance with one embodiment of the present invention.

In one non-limiting example, each of the plurality of bands 12, 14, 16 may include a natural rubber or elastic material 11, that is covered with a resilient or stretchable fabric material 13, as better illustrated in FIG. 1A. FIG. 1A shows a cross-sectional view of the braided goggle strap 10, showing bands 12, 14, 16 each including an elastic material 11 that is covered or enclosed by a resilient fabric material 13. The resilient fabric material 13 protects the individual elastic or rubber material 11 from deteriorating due to exposure to sunlight, chemicals, UV light, salt, or other elements. The resilient fabric material 13 is designed to expand and contract along with the expansion of the elastic material 11. The resilient fabric material 13 may include any woven or nonwoven material, cotton, polyester, nylon, poly-vinyl chloride (PVC), rayon, microfiber, acrylic, acetate, wool, leather, vinyl, or any other suitable fabric that is able to withstand wear and tear and repeated stretching over time. In the preferred embodiment, the stretchable fabric 13 comes in a variety of different colors and/or patterns. For example, a braided goggle strap 10 may include a first band 12 having a blue fabric covering, a second band 14 having a black fabric covering, and a third band 16 having a light blue fabric covering. Colored fabrics provide a benefit of being able to locate and identify swimming goggles 30 if lost in a pool or pond, and can help distinguish and identify one braided goggle strap 10 from another braided goggle strap 10 or from other conventional goggle straps. The colors selected may include bright, florescent colors that are easily visible under water. Also, one or more bands 12, 14, 16 may include indicia, letters, characters, symbols, or ornaments that is printed or attached to the outer resilient fabric material 13.

Each band 12, 14, 16 includes three basic dimensions comprising length, width and thickness. The dimensions may be selected to provide a braided goggle strap 10 that is adapted for use with all types of goggles and that can be used in a variety of different environments. In one exemplary embodiment, each band 12, 14, 16 is 30 inches in length, ⅛ inch wide, and 1/16 of an inch thick. Bands 12, 14, 16 are braided together to form a flat, resilient, braided goggle strap 10 having an approximate length, as depicted in a relaxed, non-stretched state, of 30 inches in length, ¼ of an inch wide, and 1/16 of an inch thick. The total width of the braided goggle strap 10 is slightly smaller than the width of aperture tabs or strap slots that are provided at opposite, outer edges of protective goggles and swimming goggles. Many protective goggles and swimming goggles include aperture tabs or strap slots that are situated along the outer edge of eye cups, as better illustrated in FIG. 2. Each strap slot 32, 34 is configured to receive the braided goggle strap 10 so attach the swimming goggles 30 onto the head of a user. Thus, the combinational width of each band 12, 14, 16 is optimally selected to provide a braided strap 10 having a total width that is slightly smaller than typical strap slots 32, 34 found on swimming goggles 30.

With continued reference to FIG. 1, the flat, resilient, braided goggle strap 10 includes a pair of extensions or guides for threading the braided strap 10 through each strap slot 32, 34 of the swimming goggles 30. In the preferred embodiment, the pair of extensions comprise a first eye loop 22 disposed at the first end 18 of the strap 10, and a second eye loop 24 disposed at the second end 20 of the strap 10, opposite the first end 18. Each eye loop 22, 24 is dimensionally constructed and sized to pass through a first strap slot 32, and a second strap slot 34, respectively, of swimming goggles 30, as better illustrated in FIG. 2. Each eye loop 22, 24 is formed using extended sections of two bands 12 and 14. To better illustrate, bands 12, 14, 16 are braided together such that one end of one band 12 terminates at a second end 20 of the braided strap 10 while an opposite end of the one band 12 extends outwards a length from a first end 18 of the braided strap 10. In addition, one end of a second band 14 terminates at the first end 18 of the braided strap 10 while an opposite end of the second band 14 extends outwards a length from the second end 20 of the braided strap 10. The two opposite ends of band 16 are configured to terminate at both the first end 18 and the second end 20. Each band extension of bands 12, 14 is folded over and securely sealed along the ends 18, 20 using adhesive, bonding or stitching techniques to form a pair of eye loops 22 and 24. Thus, by using a portion of the already existing bands 12, 14 to form eye loops 22, 24, there eliminates the need of having to implement additional materials which helps reduce costs and time required in constructing the braided goggle strap 10. The beneficial feature of eye loops 22, 24 is to help guide the two opposite ends of the braided goggle strap 10 through a pair of strap slots 32, 34 typically provided on swimming goggles 30. The formed eye loops 22, 24 help eliminate fraying as often seen on the ends of non-looped extensions.

It will be understood that eye loops 22, 24 can be separately added to the ends 18, 20 of the braided goggle strap 10 using any well-known methods or techniques. Also, in one alternative embodiment, a rigid member 19, 21 or stiffening member may be incorporated within, disposed on, or attached to each eye loop 22, 24 to provide a rigid eye loop 22, 24 that will not bend or flex out of proportion when a user attempts to thread the eye loops 22, 24 through each strap slot 32, 34 on a pair of goggles or swimming goggles 30. Further, in one alternative embodiment, eye loops 22, 24 may be replaced with a plastic, hard rubber, or vinyl element that can be used to thread the braided goggle strap 10 through each slot 32, 34.

Figure 1B:
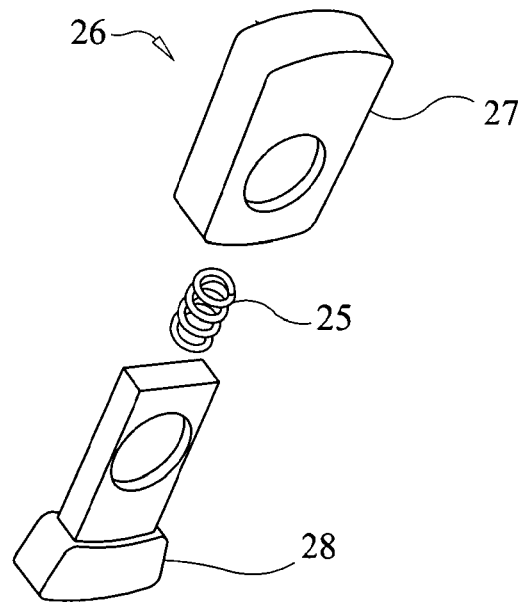
FIG. 1B is an exploded, perspective view of a bias fastener including a bias member defined by a spring, in accordance with the present invention.

As illustrated in FIG. 1, the flat, resilient, braided goggle strap 10 also includes a bias fastener 26 that is used for selectively adjusting the length of the braided strap 10 to securely tighten or loosen the swimming goggles 30 onto user's head. In the preferred embodiment, bias fastener 26 comprises a spring-biased fastener having an outer body 27 including an opening and an outer body aperture formed through the outer body. The bias fastener 26 also includes an inner body 28 shaped and sized to slide within the opening of the outer body 27 where an inner body aperture is formed through the inner body 28. The inner body 28 also includes a stopper (not shown) formed adjacent a lower section of the inner body aperture to prevent the inner body 28 from falling out of the opening of the outer body 27 when the inner body 28 is securely inserted within the outer body 27. As better illustrated in FIG. 1B, the bias fastener 26 further includes a bias member 25 defined by a spring. The spring 25 is operatively disposed between the outer body 27 and the inner body 28 to naturally urge the two bodies 27, 28 apart from each other resulting in the outer and inner body apertures to misalign with each other. The misaligned body apertures grip or lock onto the braided goggle strap 10 to prevent the strap from moving freely there through.

In use, the bias fastener 26 is held between a thumb and index finger of one hand, and a compressing force is applied to both bodies 27, 28. The pressure forces the inner body 28 to slide within the outer body 27 and compress the spring to allow the body apertures of each body 27, 28 to align with each other forming a strap hole 29. Thus, the braided strap 10 freely travels through strap hole 29 when both body apertures are in alignment. To lock the fastener 26 onto the braided goggle strap 10, the user simply releases the fastener 26 where the spring pushes the inner body 28 away from the outer body 27 to cause the body apertures to become misaligned. In one alternative embodiment, bias fastener 26 may include an outer body 27 and an inner body 28 each having two body apertures where each body aperture receives opposite ends of the braided goggle strap 10.

Though the preferred embodiment discloses a spring-biased fastener 26, other types of fasteners may also be used with the braided goggle strap 10 without departing from the scope of the invention. For example, bias fastener 26 may include a quick release buckle, a ratchet-type fastener, snaps, clips, clamps, hook and loop attachments, an adjustable clasp, squeeze release buckle, clip buckle, snap buckle, ratchet buckle, slider, or any other suitable mechanism used for making adjustments.

Figure 2:
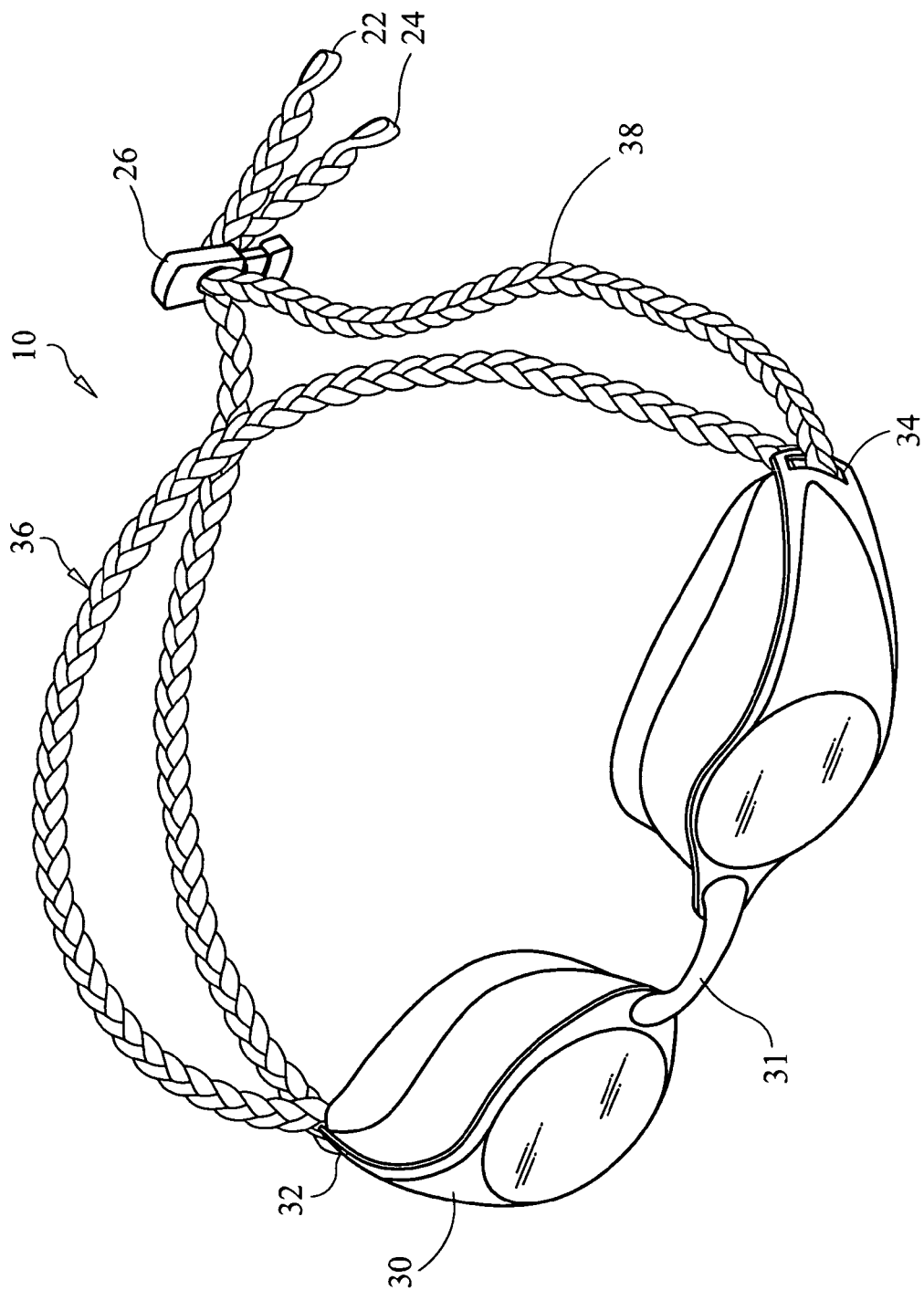
FIG. 2 is a perspective view of the braided goggle strap of FIG. 1, shown attached to a pair of swimming goggles, in accordance with the present invention.

Turning now to FIG. 2 there is shown a perspective view of the braided goggle strap 10 securely attached to a pair of swimming goggles 30. In the illustrative embodiment, a pair of swimming goggles 30 includes a pair of transparent or tinted eye cups each shaped to conform to the eyes of a wearer. Each eye cup generally includes a foam or padded material disposed along the peripheral edge of the cup to provide comfort around the area of the eyes. For illustrative purposes, the pair of swimming goggles 30 includes a pair of eye cups that are coupled together via, a nose bridge 31. It is contemplated that the braided goggle strap 10 of the present invention is adapted for use with a variety of different swimming goggles and not only with swimming goggles 30, as demonstrated herein. Typically, swimming goggles 30 include a tab with an aperture or a first strap slot 32 provided at the outer edge of one eye cup, and second tab with an aperture or a second strap slot 34 provided at the outer edge of another eye cup. Strap slots 32, 34 correspondingly align with each other, along a horizontal plane, and are dimensionally sized to securely receive the flat braided goggle strap 10.

To attach the braided goggle strap 10 to a pair of swimming goggles 30, a user first removes the bias fastener 26 if situated onto the braided strap 10. The user simply holds a first eye loop 22 between an index finger and thumb of one hand and inserts the eye loop 22 through a first strap slot 32 of the swimming goggle 30. The user pulls the first eye loop 22 through the strap slot 32 until a sufficient length of braided strap 10 is achieved. The user proceeds to do the same with the second eye loop 24 by sliding the second eye loop 24 through the second strap slot 34 of swimming goggles 30. The user pulls the second eye loop 24 through the strap slot 34 until a sufficient length of braided strap 10 is achieved. Thus, each eye loop 22, 24 is easily held between a thumb and index finger of one hand and threaded through a corresponding strap slot 32, 34 with ease. Eye loops 22, 24 are adapted to help guide the braided goggle strap 10 through each strap slot 32, 34 of the swimming goggles 30.

In attaching the bias fastener 26 to the braided goggle strap 10, the user simply holds the fastener 26 in one hand and compresses both bodies 27, 28 toward each other to overcome the spring bias provided by the spring. The compressed force allows the body apertures to align with each other forming strap hole 29. Both eye loops 22, 24 are easily inserted within strap hole 29 until a desired length of each end of the braided strap 10 has passed through the strap hole 29. The bias fastener 26 is then released allowing the bias fastener 26 to securely engage the braided strap 10. As better illustrated in FIG. 2, the braided goggle strap 10 is threaded through each strap slot 32, 34, of the swimming goggles 30, to form a first attachment strap 36 and a second attachment strap 38 both used for securing the swimming goggles 30 to a user's head 40.

Figure 3:
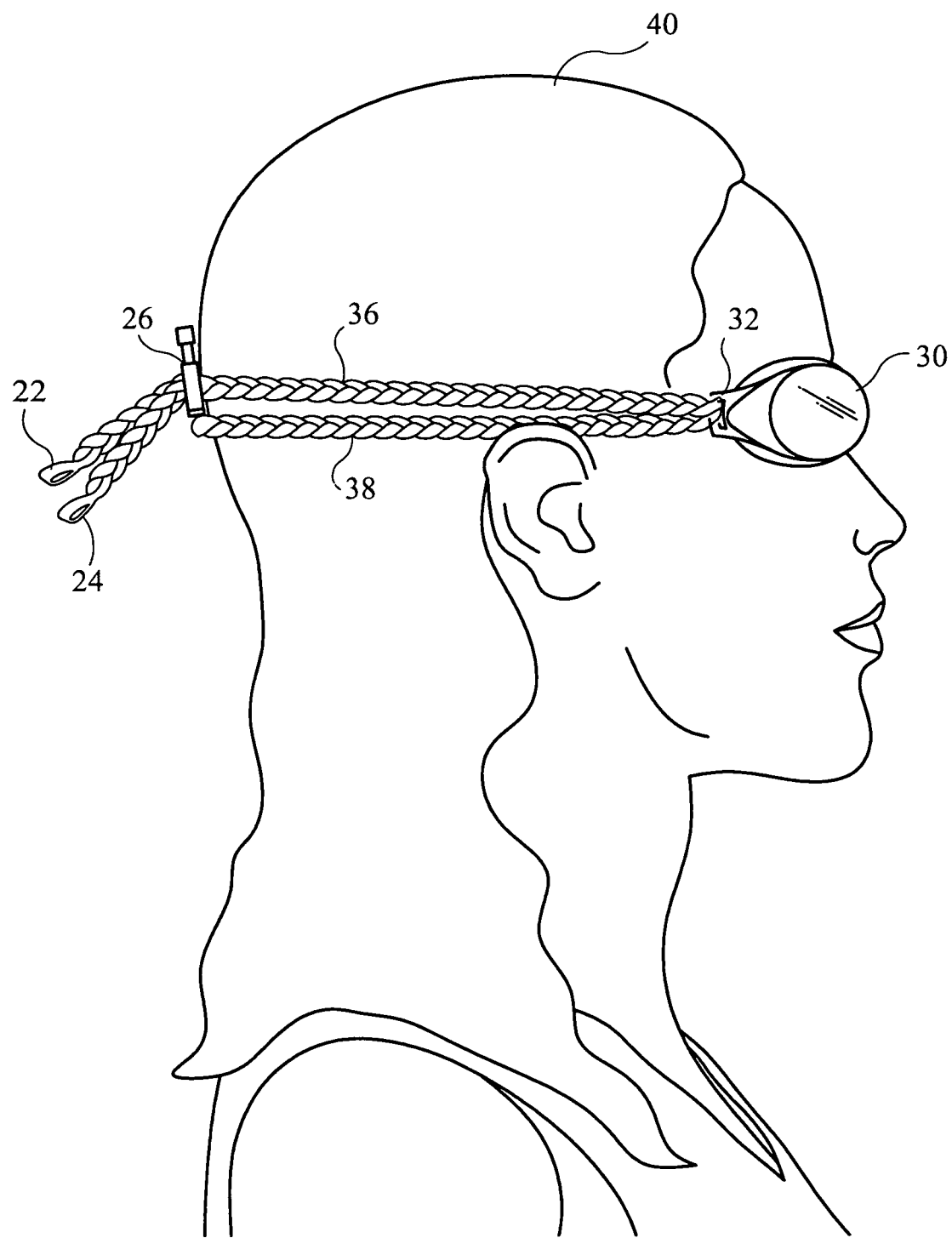
FIG. 3 is a side view of the braided goggle strap of FIG. 1, shown attached onto a user's head.

FIG. 3 shows a side view of a pair of swimming goggles 30 securely attached onto the head 40 of a user. In preparation for swimming, a user initially positions the swimming goggles 30 comfortably over the eyes with one hand, and stretches both attachments straps 36, 38 over the head 40. The user may operate the bias fastener 26 to tighten the braided goggle strap 10 onto the head 40 for securing the swimming goggles 30 in place. The fastener 26 allows a user to quickly make adjustments while the braided goggle strap 10 is situated on the user's head. This alleviates the need of having to remove the swimming goggles 30 off the user's head every time the person wishes to make adjustments during use.

Further, in one alternative embodiment, the flat, resilient, braided goggle strap 10 may include one or more attachments or loops that are integrally formed with the braided goggle strap 10 and used to attach or secure items to the braided strap 10. For example, the braided strap 10 may include a stretchable loop integrally formed with or separately attached to the strap 10 to securely hold a snorkel to the braided goggle strap 10. Also, one or more pads or foam slip-ons (not shown) may be attached to a section of each loop strap 36, 38 to provide a padded cushion to the back of the head 40 when the braided goggle strap 10 is worn.

The present invention provides a flat, resilient braided goggle strap 10 that includes a plurality of bands 12, 14, 16 braided together to form a strong, comfortable strap when compared to conventional goggle straps. The braided bands 12, 14, 16 provide superior mechanical properties due to fiber orientations along three directions. The braided goggle strap 10 includes a resilient or stretchable fabric material that does not stick to a user's hair like a rubber strap does, and includes a flat geometric shape that does not travel or roll along the outer surface of a user's head as with tubular bungee cord straps. The flat braided composite provides a goggle strap 10 that fits comfortably on a user's head and does not have to be overly tightened in order to prevent the braided strap 10 from rolling or twisting on the user's head.

Further, the flat, resilient braided goggle strap 10 of the present invention is designed to provide uniaxial tensile strength, even stress distribution, and minimal sinusoidal stress when worn by a user. The plurality of bands 12, 14, 16 are braided together to provide superior mechanical strength forming a braided goggle strap 10 that is harder to break and able to withstand prolonged use, and exposure to sunlight, chemicals, and stress. As a flat non-tubular member, the braided goggle strap 10 surpasses the tubular bungee strap's poor sheer resistance and limited strength in the primary loading direction. The braided goggle strap 10 is configured to evenly distribute tension and firmly secure eyewear, such as swimming goggles, comfortably onto a user's head.

As variations, combinations and modifications may be made in the construction and methods herein described and illustrated without departing from the scope of the invention, it is intended that all matter contained in the foregoing description or shown in the accompanying drawings shall be interpreted as illustrative rather than limiting. Thus, the breadth and scope of the present invention should not be limited by any of the above-described exemplary embodiments, but defined in accordance with the foregoing claims appended hereto and their equivalents.

What I claim is:

1. A braided goggle strap comprising:
   a plurality of bands braided together to form a braided elongated body having a first end and a second end opposite said first end, each of said plurality of bands including a resilient material having a resilient fabric covering;
   a first band extension being a portion of one of said plurality of bands and extending a length from said first end;
   a second band extension being a portion of another one of said plurality of bands and extending a length from said second end, said first band extension folded over and attached to said first end forming a first eye loop, and said second band extension folded over and attached to said second end forming a second eye loop, each of said eye loops and each of said plurality of bands having a width dimensioned to removeably pass through a pair of apertures provided on a pair of goggles; and
   a bias fastener operated to releasably grip onto said plurality of bands for securely attaching said braided goggle strap onto a user's head.

2. The braided goggle strap of claim 1, wherein said plurality of bands include a first band, a second band, and a third band, each of said bands having a flat geometric shape and braided together to form said braided goggle strap having a flat geometric shape and width to pass through said pair of apertures on said pair of goggles.

3. The braided goggle strap of claim 2, wherein said resilient material includes anyone of natural rubber, synthetic rubber, latex, nylon, stretch fabric (elastomerics), blended rubber with polyester, blended rubber with cotton, blended rubber with nylon or any combination thereof.

4. The braided goggle strap of claim 3, wherein said resilient fabric covering includes any one of woven or nonwoven material, cotton, polyester, nylon, poly-vinyl chloride (PVC), rayon, microfiber, acrylic, acetate, wool, leather, vinyl, or any other suitable fabric that is able to withstand wear and tear and repeated stretching and contracting over time.

5. The braided goggle strap of claim 4, wherein a distal end of said first band extension, and a distal end of said second band extension are each attached to said first end and second end, respectively, using anyone of an adhesive, glue, contact cement, sewing, stitching heat bonding, or welding to define said first eye loop and said second eye loop.

6. The braided goggle strap of claim 5, wherein said bias fastener includes an outer body having an opening and an outer body aperture, an inner body dimensioned to slideably fit within said opening of said outer body and including an inner body aperture, and a bias member disposed within said opening and between said outer body and said inner body, where said bias member operatively separates said outer body from said inner body to misalign said body apertures to releasably grip said plurality of bands when said plurality of bands are inserted through said body apertures.

7. The braided goggle strap of claim 6, wherein each of said first eye loop and said second eye loop includes a rigid member, said rigid member being attached to, or enclosed within each of said eye loops to provide a first rigid eye loop and a second rigid eye loop that will not bend or flex when said eye loops are inserted through said respective apertures of said pair of goggles.

8. The braided goggle strap of claim 6, wherein said resilient fabric covering includes a same color or a variety of different colors defining a braided goggle strap including a plurality of bands having different colors.

9. A braided swimming goggle strap for use with swimming goggles, said braided swimming goggle strap comprising:
   a plurality of strands interlaced together to form said braided swimming goggle strap having opposite ends, each of said plurality of strands including a resilient material enclosed with a resilient fabric material;
   a first eye loop formed from a portion of one of said plurality of strands and extending from one of said opposite ends; a
   a second eye loop formed from a portion of said one of said plurality of strands and extending from another of said opposite ends each of said eye loops removeably insertable through a pair of apertures provided on said swimming goggles so that said braided goggle strap forms a first attachment strap and a second attachment strap; and a fastener operated to releasably grip onto said braided goggle strap for securely tightening and attaching said first attachment strap and said second attachment strap onto a user's head.

10. The braided swimming goggle strap of claim 9, wherein said resilient material includes anyone of natural rubber, synthetic rubber, latex, nylon, elastomerics, blended rubber with polyester, blended rubber with cotton, blended rubber with nylon or any combination thereof.

11. The braided swimming goggle strap of claim 10, wherein said resilient fabric material includes anyone of woven or nonwoven material, cotton, polyester, nylon, polyvinyl chloride (PVC), rayon, micro fiber, acrylic, acetate, wool, leather, vinyl, or any other suitable fabric that is able to withstand wear and tear and repeated stretching over time.

12. The braided swimming goggle strap of claim 11, wherein said fastener includes an outer body having an opening and an outer body aperture, an inner body dimensioned to slideably fit within said opening of said outer body and including an inner body aperture, and a bias member disposed within said opening and between said outer body and said inner body to misalign said body apertures and grip said plurality of strands when said plurality of strands are inserted through said body apertures, and where said fastener is operated to align said body apertures to release said grip on said plurality of strands allowing said plurality of strands to slide freely through said body apertures.

13. The braided swimming goggle strap of claim 12, wherein each of said plurality of strands comprises a flat geometric shape and are braided together to form said braided swimming goggle strap having a flattened geometric shape and width dimensioned to slide through said pair of apertures provided on said swimming goggles.

14. The braided swimming goggle strap of claim 13, wherein said resilient fabric material includes a same color or a variety of different colors to form a braided swimming goggle strap including a plurality of strands having different colors.

15. The braided swimming goggle strap of claim 14, wherein said plurality of strands comprises a first strand, a second strand, and a third strand.

16. The braided swimming goggle strap of claim 15, wherein each of said eye loops includes a rigid member affixed along a surface of said eye loop to provide a first rigid eye loop and a second rigid eye loop that will not bend or flex as said eye loops are inserted through respective apertures of said swimming goggles.

17. A resilient braided strap releasably attachable to a pair of goggles having a nose bridge disposed between a pair of eye cups and apertures disposed on peripheral edges of said eye cups, said resilient braided strap comprising:

a plurality of bands braided together to form said resilient braided strap having a first end opposite a second end, each of said plurality of bands including a planar geometric shape, and a resilient material having an outer resilient fabric comprising a same or different color, wherein one of said plurality of bands includes a first eye loop that extends from said first end, and a second eye loop that extends from said second end, each of said eye loops dimensioned to removeably extend through the apertures of the pair of goggles, said first end removeably insertable through one of said apertures, and said second end removeably insertable through another of said apertures to define a first head strap and a second head strap; and a fastener releasably biased to adjustably tighten said first head strap and said second head strap onto a user's head to secure said eye cups over both eyes of said user.

18. The resilient braided strap of claim 17, wherein said resilient material includes any of natural rubber, synthetic rubber, or elastomerics, and wherein said resilient fabric includes anyone of woven or nonwoven material, cotton, polyester, nylon, polyvinyl chloride (PVC), rayon, micro fiber, acrylic, acetate, wool, leather, or vinyl.

19. The resilient braided strap of claim 18, further including a bias fastener including an outer body having an opening and an outer body aperture, an inner body dimensioned to slideably fit within said opening of said outer body and including an inner body aperture, and a bias member disposed within said opening and between said outer body and said inner body to misalign said body apertures and releasably grip said plurality of bands when said plurality of bands are inserted through said body apertures.

* * * * *